(12) United States Patent
Yan et al.

(10) Patent No.: US 12,129,232 B2
(45) Date of Patent: Oct. 29, 2024

(54) ANTI-FOULING DISPERSANT COMPOSITION AND METHOD OF USE

(71) Applicant: BL Technologies, Inc., Minnetonka, MN (US)

(72) Inventors: Dengchao Yan, Shanghai (CN); Yongtao Shi, Shanghai (CN); Mike Hong, Shanghai (CN); Xiaofeng Tang, Shanghai (CN); Guixi Zhang, Shanghai (CN)

(73) Assignee: BL Technologies, Inc., Minnetonka, MN (US)

( * ) Notice: Subject to any disclaimer, the term of this patent is extended or adjusted under 35 U.S.C. 154(b) by 591 days.

(21) Appl. No.: 17/259,082

(22) PCT Filed: Jun. 24, 2019

(86) PCT No.: PCT/US2019/038680
§ 371 (c)(1),
(2) Date: Jan. 8, 2021

(87) PCT Pub. No.: WO2020/013978
PCT Pub. Date: Jan. 16, 2020

(65) Prior Publication Data
US 2021/0269343 A1    Sep. 2, 2021

(30) Foreign Application Priority Data

Jul. 13, 2018 (CN) .......................... 201810769623.3

(51) Int. Cl.
*C07C 7/20* (2006.01)
*C02F 5/10* (2023.01)
(Continued)

(52) U.S. Cl.
CPC ................. *C07C 7/20* (2013.01); *C02F 5/10* (2013.01); *C08G 65/00* (2013.01); *C11D 1/722* (2013.01);
(Continued)

(58) Field of Classification Search
CPC ...................................................... C07C 43/20
See application file for complete search history.

(56) References Cited

U.S. PATENT DOCUMENTS 4,029,577 A    6/1977  Godlewski et al.
4,149,983 A    4/1979  Grier et al.
(Continued)

FOREIGN PATENT DOCUMENTS

CA    1062983 A1    9/1979
CA    1079604 A1    6/1980
(Continued)

OTHER PUBLICATIONS

Machine translation of 105819578, provided by Applicant. (Year: 2016).*
(Continued)

*Primary Examiner* — Clare M Perrin
(74) *Attorney, Agent, or Firm* — Armstrong Teasdale LLP

(57) ABSTRACT

An antifouling dispersant composition having an alcohol polyoxyethylene (EO) ether (EO number 1-14), represented by the general formula (I), wherein R is an alkyl with about 3-20 carbon atoms; and n is 1-14.

8 Claims, 3 Drawing Sheets

(51) Int. Cl.
  *C08G 65/00* (2006.01)
  *C11D 1/722* (2006.01)
  *C02F 103/02* (2006.01)
  *C11D 1/72* (2006.01)
  *C11D 3/28* (2006.01)

(52) U.S. Cl.
  CPC .... *C02F 2103/023* (2013.01); *C02F 2303/20* (2013.01); *C02F 2303/22* (2013.01); *C02F 2305/00* (2013.01); *C11D 1/72* (2013.01); *C11D 3/28* (2013.01)

(56) References Cited

U.S. PATENT DOCUMENTS

| | | | |
|---|---|---|---|
| 4,233,174 A * | 11/1980 | Sheridan | C11D 1/8255 134/40 |
| 4,277,257 A | 7/1981 | Matsuura et al. | |
| 4,288,327 A | 9/1981 | Godlewski et al. | |
| 5,272,226 A * | 12/1993 | Lancaster | C08G 8/28 525/507 |
| 5,427,690 A | 6/1995 | Rowe et al. | |
| 5,445,743 A | 8/1995 | Rowe et al. | |
| 6,100,227 A | 8/2000 | Burlew | |
| 6,369,010 B1 * | 4/2002 | Dreisbach | C09D 9/04 510/213 |
| 8,591,725 B2 | 11/2013 | Sundaram et al. | |
| 8,604,140 B2 | 12/2013 | Nagai et al. | |
| 9,452,957 B2 | 9/2016 | Senetar et al. | |
| 9,777,248 B2 * | 10/2017 | Masters | C11D 1/835 |
| 9,969,925 B2 * | 5/2018 | Zhang | C09K 8/52 |
| 2004/0079392 A1 | 4/2004 | Kuechler et al. | |
| 2006/0096617 A1 | 5/2006 | Kuechler et al. | |
| 2017/0183248 A1 | 6/2017 | Leen et al. | |

FOREIGN PATENT DOCUMENTS

| | | | |
|---|---|---|---|
| CA | 2769412 | C | 2/2015 |
| CN | 1594383 | A | 3/2005 |
| CN | 1694857 | A | 11/2005 |
| CN | 1325447 | C | 7/2007 |
| CN | 101012411 | A | 8/2007 |
| CN | 101368141 | A | 2/2009 |
| CN | 101397527 | A | 4/2009 |
| CN | 102405917 | A | 4/2012 |
| CN | 103108942 | A | 5/2013 |
| CN | 103224841 | A | 7/2013 |
| CN | 104120439 | A | 10/2014 |
| CN | 105084319 | A | 11/2015 |
| CN | 105777473 | A | 7/2016 |
| CN | 105819578 | A * | 8/2016 |
| CN | 106103391 | A | 11/2016 |
| CN | 106145395 | A | 11/2016 |
| CN | 106542589 | A | 3/2017 |
| CN | 106643276 | A | 5/2017 |
| CN | 106745857 | A | 5/2017 |
| CN | 109486562 | A | 3/2019 |
| EP | 0445074 | A1 | 9/1991 |
| EP | 1897908 | B1 | 1/2009 |
| EP | 1562881 | B1 | 1/2012 |
| EP | 2566937 | A2 | 3/2013 |
| JP | 855111439 | A | 8/1980 |
| WO | 1999057061 | A1 | 11/1999 |
| WO | 2004040039 | A2 | 5/2004 |
| WO | 2010114928 | A2 | 10/2010 |
| WO | 2011138305 | A2 | 11/2011 |

OTHER PUBLICATIONS

Office Action and Search Report issued in Chinese Application No. 201810769623.3, with English translation, dated Apr. 8, 2022, 14 pages.

PCT International Search Report and Written Opinion, Application No. PCT/US2019/038680, dated Sep. 27, 2019, 12 pps.

Office Action and Search Report issued in Chinese Application No. 201810769623.3, with English translation, dated Oct. 10, 2022, 15 pages.

"Rhodasurf 870", Chemlink Specialties Product List, accessed online on Aug. 9, 2023 at URL: https://www.chemlink.co.uk/product-list/#1498766385989-c0a7eaf0-ec84.

Office Action and Search Report issued in Tawainese Patent Application No. 108123626, dated Aug. 4, 2023, 8 pages.

* cited by examiner

ANTI-FOULING DISPERSANT COMPOSITION AND METHOD OF USE

CROSS-REFERENCE TO RELATED APPLICATIONS

This application is a national phase of International Patent Application No. PCT/US2019/038680 filed Jun. 24, 2019, which claims the priority benefit of Chinese Patent Application Serial No. 201810769623.3 filed Jul. 13, 2018, the entireties of which are incorporated herein by reference.

FIELD OF INVENTION

The disclosed technology generally described hereinafter provides for an antifouling dispersant composition and method to reduce fouling in olefin production processes and systems therein, and more specifically, an antifouling dispersant composition and method to reduce fouling in a methanol-to-olefin (MTO) water washing system, wherein the composition comprises an alcohol polyoxyethylene (EO) ether (EO number 1-14).

BACKGROUND OF THE INVENTION

It is well known that in olefin production systems, fouling is a phenomenon that may significantly limit the performance of the individual components, and therefore the entire operation of the olefin production unit, such as ethylene, propylene, isoprene, chloroprene, butylene (and isomers thereof), isobutylene, and butadiene production. Fouling control and prevention are, therefore, very critical, and several methods have been used to accomplish this goal.

Generally, olefin is produced commercially by the steam or catalytic cracking of a wide range of hydrocarbon feedstocks. Ethylene is obtained mainly from cracking naphtha, gas, oil and condensates with the coproduction of propylene, C4 olefins and aromatics.

Specifically, in a methanol-to-olefin (MTO) water washing system, an MTO reactor produces light olefins and some hydrocarbon byproducts, such as aromatic hydrocarbons including hexamethylbenzene, pentamethylbenzene, tetramethylbenzene, etc. However, these hydrocarbon byproducts are strong hydrophobic compounds and will settle down in the water washing tower to cause serious fouling issues. The organic foulants in MTO water washing systems are comprised of hexamethylbenzene as major component, and some minor components such as pentamethylbenzene, tetramethylbenzene, etc. These foulants will cause an efficiency reduction of the water washing tower, reduce its run length and induce negative impacts on olefin production.

Therefore, what is needed in the art is an antifouling dispersant composition and method to effectively eliminate the serious fouling problems experienced in these olefin production processes, and more specifically, in an MTO water washing tower system.

SUMMARY OF THE INVENTION

The disclosed technology generally described hereinafter provides for an antifouling dispersant composition and method to effectively eliminate the serious fouling problems in olefin production processes and systems therein.

In other embodiments, a composition and method for an antifouling dispersant composition and method to effectively eliminate the serious fouling problem in an MTO water washing tower system is provided.

According to one aspect of the disclosed technology, an antifouling dispersant composition is provided. The antifoulant dispersant composition comprising: an alcohol polyoxyethylene (EO) ether (EO number 1-14), represented by the general formula

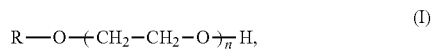

wherein R is an alkyl with about 3-20 carbon atoms; and n is 1-14.

In some embodiments, the antifoulant dispersant further comprises water and/or one or more organic solvents. In some embodiments, the composition comprises about 0-95% water. In some embodiments, the composition comprises about 0-95% organic solvent. In some embodiments, the organic solvent comprises an alcohol, a glycol, a glycol ether, a glycerol, or a pyrrolidinone.

In some embodiments, the organic solvent comprises methanol, ethanol, isopropanol, ethylene glycol, propylene glycol, ethylene glycol monomethyl ether, ethylene glycol monoethyl ether, ethylene glycol monopropyl ether, ethylene glycol monobutyl ether, diethylene glycol, diethylene glycol monomethyl ether, diethylene glycol monoethyl ether, diethylene glycol monopropyl ether, diethylene glycol monobutyl ether, glycerol, triethylene glycol, 1-methyl-2-pyrrolidinone, or a combination thereof.

In some embodiments, the antifoulant dispersant composition further comprises one or more alkyl phenolic resin ethoxylates, represented by the general formula

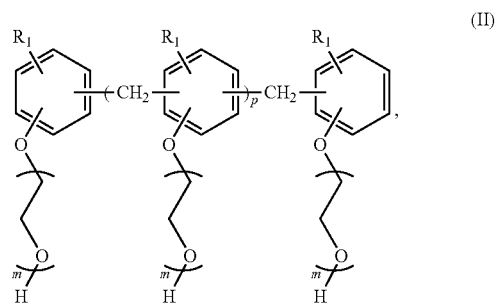

wherein, $R_1$ is C3-C18 alkyl, the ethoxylate group (EO) number m is at a range of 1-50, and the resin polymerization degree p is at a range of 0-20. In some embodiments, the composition comprises about 0-60% alkyl phenolic resin ethoxylate.

In some embodiments, the composition comprises about 0-60% alkyl phenolic resin ethoxylate. In some embodiments, the antifoulant dispersant composition comprises about 0-95% water, about 0-95% of an organic solvent, and 0-60% of an alkyl phenolic resin ethoxylate. In some embodiments, the composition has a freezing point of less than about −25° C.

In yet another aspect of the disclosed technology, a method of reducing fouling in olefin production system is provided. The method comprises adding an antifouling dispersant composition to an olefin production system, the antifouling dispersant composition comprising an alcohol polyoxyethylene (EO) ether (EO number 1-14), represented by the general formula

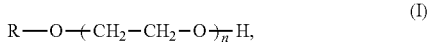

wherein R is an alkyl with about 3-20 carbon atoms; and n is 1-14.

In some embodiments, the olefin production system comprises ethylene, propylene, isoprene, chloroprene, butylene (isomers thereof), isobutylene and butadiene, or a methanol-to-olefin (MTO) water washing system. In some embodiments, about 1-1000 ppm of the antifouling dispersant composition is added to a methanol-to-olefin (MTO) water washing tower. In some embodiments, the antifouling dispersant composition is continuously or intermittently injected into the MTO water washing tower. In some embodiments, the antifouling dispersant composition further comprises water and/or one or more organic solvents.

In some embodiments, the antifouling dispersant composition comprises about 0-95% water. In some embodiments, the antifouling dispersant composition comprises about 0-95% organic solvent. In some embodiments, the organic solvent comprises an alcohol, a glycol, a glycol ether, glycerol, or a pyrrolidinone.

In some embodiments, the method further comprises one or more alkyl phenolic resin ethoxylates, represented by the general formula

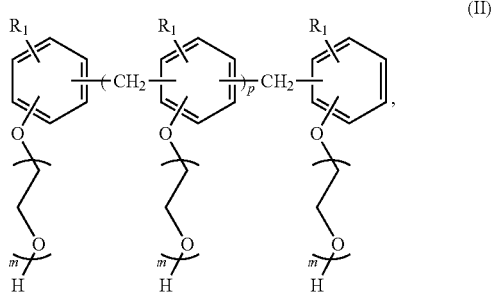

wherein, $R_1$ is C3-C18 alkyl, the ethoxylate group (EO) number m is at a range of 1-50, the resin polymerization degree p is at a range of 0-20.

BRIEF DESCRIPTION OF THE DRAWINGS

These and other features of the disclosed technology, and the advantages, are illustrated specifically in embodiments now to be described, by way of example, with reference to the accompanying diagrammatic drawings, in which.

DETAILED DESCRIPTION OF EXEMPLARY EMBODIMENTS

Figure 1:
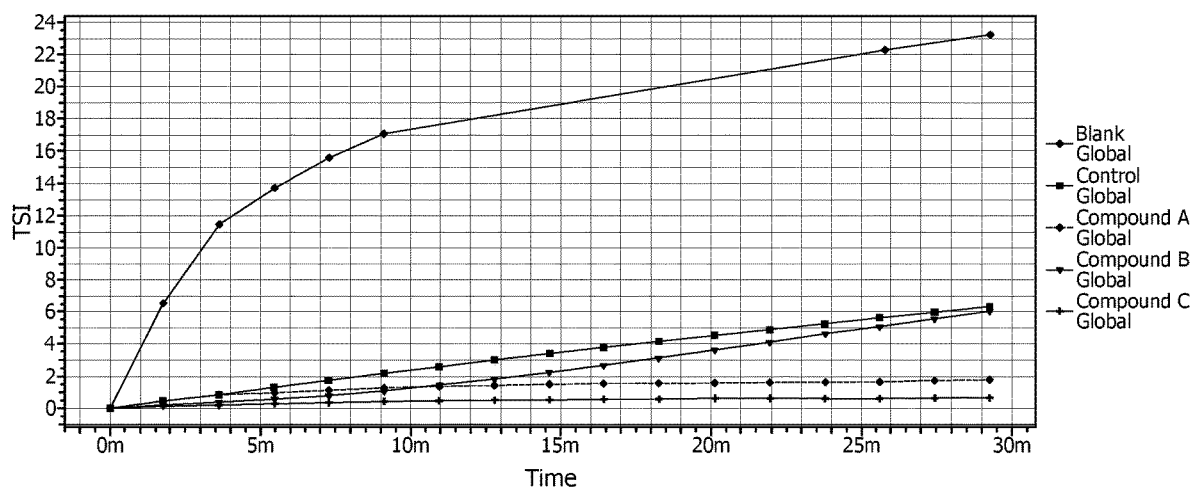
FIG. 1 is a graph providing results of an illustrative embodiment of the disclosed technology.

The disclosed technology generally described hereinafter provides for an antifouling dispersant composition and method to effectively eliminate the serious fouling problems observed in olefin production processes and systems therein. For example, the ethylene production processes and systems include, but are not limited to, hydrocarbon cracking systems, process gas compressor systems, and MTO water washing tower systems. The antifouling dispersant composition effectively inhibits the fouling formation and removal of foulants in such systems to extend run length and ensure smooth operation. In some embodiments, the antifoulant dispersant composition inhibits fouling formation and removal of foulants in an MTO water washing tower to extend its run length and ensure smooth MTO operation.

The present technology provides for an antifouling dispersant composition. The antifouling dispersant composition is stable, especially in the MTO process without any degradation, which ensures consistent effective antifouling performance. The antifouling dispersant composition is soluble in water and will not produce any contaminants within an ethylene production process or the MTO production process, which is beneficial because it provides good system compatibility due to the minimum contribution of impurities to process streams, while allowing for an extension of production run length as a result of effective fouling control. The antifouling dispersant composition additionally provides universal applicability, as the composition can achieve an extremely low freezing point of less than about −25° C. The extremely low freezing point of the composition provides beneficial convenient operational advantages for MTO plants, especially on cold days. MTO plants are commonly located in remote areas and where there is mostly no heating for the dispersant storage area, tanks and pipelines for dosing. Current products available on the market indicate higher freezing point, which will cause product freezing issues, phase separation issues, too high viscosity to feed on cold days, and sequentially cause MTO production issues, such as production fluctuation, fouling, unplanned shutdown, etc.

In some embodiments, the antifouling dispersant composition of the present technology comprises an alcohol polyoxyethylene (EO) ether (EO number 1-14), represented by the general formula

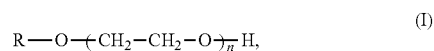

wherein R is an alkyl with about 3-20 carbon atoms; and n is 1-14. The EO number represents the number of ethylene oxide units. The EO number is significant as it provides good dispersant efficacy to inhibit fouling, as well as MTO organic fouling.

In some embodiments, the antifouling dispersant composition further comprises water and/or one or more organic solvents. In some embodiments, the composition comprises about 0-95% water, in other embodiments, about 10-80% water, in other embodiments, about 15-70% water, and in other embodiments, about 20-60% water.

In some embodiments, the antifouling dispersant composition comprises about 0-95% organic solvent, in some embodiments, about 10-80% organic solvent, in other embodiments, about 15-70% organic solvent, and in other embodiments, about 20-60% solvent.

In some embodiments, the organic solvent comprises an alcohol, a glycol, a glycol ether, glycerol, or a pyrrolidinone. In some embodiments, the organic solvent comprises methanol, ethanol, isopropanol, ethylene glycol, propylene glycol, ethylene glycol monomethyl ether, ethylene glycol monoethyl ether, ethylene glycol monompropyl ether, ethylene glycol monobutyl ether, diethylene glycol, diethylene glycol monomethyl ether, diethylene glycol monoethyl ether, diethylene glycol monompropyl ether, diethylene glycol monombutyl ether, glycerol, triethylene glycol, 1-methyl-2-pyrrolidinone, or a combination thereof.

In some embodiments, the antifouling dispersant composition further comprises one or more alkyl phenolic resin ethoxylates, represented by the general formula

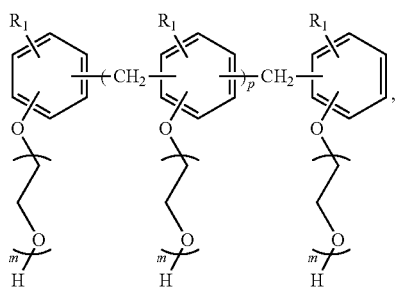

wherein, $R_1$ is C3-C18 alkyl, the ethoxylate group (EO) number m is at a range of 1-50, and the resin polymerization degree p is at a range of 0-20.

In some embodiments, the antifouling dispersant composition comprises about 0-60% alkyl phenolic resin ethoxylate, in other embodiments, about 10-50% alkyl phenolic resin ethoxylate, and in other embodiments, about 15-45% alkyl phenolic resin ethoxylate.

In some embodiments, the antifouling dispersant composition comprises about 0-95% water, about 0-95% of an organic solvent, and 0-60% of an alkyl phenolic resin ethoxylate.

The present technology further provides for a method of reducing fouling in a methanol-to-olefin (MTO) water washing system. The method comprises adding an antifouling dispersant composition to a methanol-to-olefin (MTO) water washing tower, the antifouling dispersant composition comprising an alcohol polyoxyethylene (EO) ether (EO number 1-14), represented by the general formula

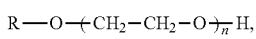

wherein R is an alkyl with about 3-20 carbon atoms; and n is 1-14.

In some embodiments, the antifouling dispersant composition comprises about 1-1000 ppm of the antifouling dispersant composition is added to the methanol-to-olefin (MTO) water washing tower.

In some embodiments, the antifouling dispersant composition is continuously injected into an MTO water washing tower. Continuously feeding of the antifouling dispersant composition is preferred to effectively disperse small particles, prevent them to aggregate into bigger size particles and inhibit the foulants to settle down in MTO water washing system. In other embodiments, the antifouling dispersant composition is intermittently injected into the MTO water washing tower. Intermittently feeding of the antifouling dispersant composition is acceptable to inhibit the fouling in MTO water washing system. The water recirculation of MTO water washing system is recommended if intermittently feeding of the antifouling dispersant composition.

EXAMPLES

The present invention will be further described in the following examples, which should be viewed as being illustrative and should not be construed to narrow the scope of the invention or limit the scope to any particular invention embodiments.

Systematic lab work was conducted to evaluate the performance of some compounds. The results confirmed enhanced performance of the antifouling dispersant and composition to effectively disperse the fouling materials, as compared with a market-in-use product.

Procedure

A hexamethylbenzene (HMB)/acetone solution as 3.125% (wt %) HMB was prepared. The market-in-use dispersant sample or dispersant candidates, and compositions of the disclosed technology were diluted in deionized water, as dispersant stock solution at 1% concentration. About 0.22 g of HMB/acetone was added above into 20 g of deionized water to prepare a simulated HMB scale solution. This simulated HMB scale solution contained about 340 ppm HMB and 10532 ppm acetone in water, and was mixed well. This solution was marked as "Blank". About 0.41 g of 1% market-in-use dispersant solution above was added into 20 g of deionized water and mixed well, calculated at ~200 ppm of dispersant as product. Subsequently, about 0.225 g of HMB/acetone solution above was added, and mixed well. This solution is marked as "Control". Add calculated weight of 1% concentration solution of dispersant candidates and compositions of this disclosed technology above into 20 g of deionized water and mixed well. About 0.225 g of HMB/acetone solution above was added, and mixed well. These solutions are marked as "Compound X" or "Formulation X". Observe the HMB dispersion stability and scan the solution with Turbiscan tower (test temperature 50C). The Turbiscan test enables fast and sensitive identification of destabilization mechanisms (flocculation, coalescence, sedimentation, creaming, etc.) of dispersion/emulsion solutions. The temperature controlled measurement cell of Turiscan unit allows either to monitor dispersions/emulsions stability at specific storage temperature or to accelerate destabilization process of dispersions/emulsions. TSI (Turbiscan Stability Index) indicates the destabilization trend of dispersions/emulsions. The lower value of TSI, the better stability of dispersions/emulsions.

Example 1

Table 1 provides a comparison on chemicals:

TABLE 1

| Chemical | Dosage |
| --- | --- |
| Blank (Comparative Example 1) | 0 ppm as dispersant |
| Control (Comparative Example 2) | 200 ppm as dispersant product |
|  | (40 ppm as dispersant active) |
| Compound A | 25 ppm as dispersant active |
| Compound B | 25 ppm as dispersant active |
| Compound C | 25 ppm as dispersant active |

Compound A is a fatty alcohol (C14-C20) polyoxyethylene ether (EO 8~12). Compound B is a fatty alcohol (C3-C8) polyoxyethylene ether (EO 10~14). Compound C is a fatty alcohol (C10-C16) polyoxyethylene ether (EO 3~7).

As shown in FIG. 1, the results indicate the antifouling dispersant compounds (A, B, C) in this invention can effectively disperse the fouling materials HMB. The results indicate much better performance of the antifouling dispersant compounds (A, B, C) in this invention to effectively disperse the fouling materials HMB at lower dispersant dosage, compared with the control (Comparative Example 2).

Example 2

Table 2 provides a comparison on dispersant products:

TABLE 2

| Chemical | Dosage |
|---|---|
| Blank (Comparative Example 1) | 0 ppm as dispersant |
| Control (Comparative Example 2) | 200 ppm as dispersant product |
| Formulation 1 | 100 ppm as dispersant product |
| Formulation 2 | 50 ppm as dispersant product |

Formulation 1 is a composition of 20% fatty alcohol (C10-C16) polyoxyethylene ether (EO 3~7), 35% water and 45% ethylene glycol. Formulation 2 is a composition of 15% fatty alcohol (C14-C20) polyoxyethylene (EO 8~12) ether, 10% nonyl phenolic resin ethoxylate (m=12, p=8), 15% water, 20% ethylene glycol and 40% ethylene glycol monobutyl ether.

Figure 2:
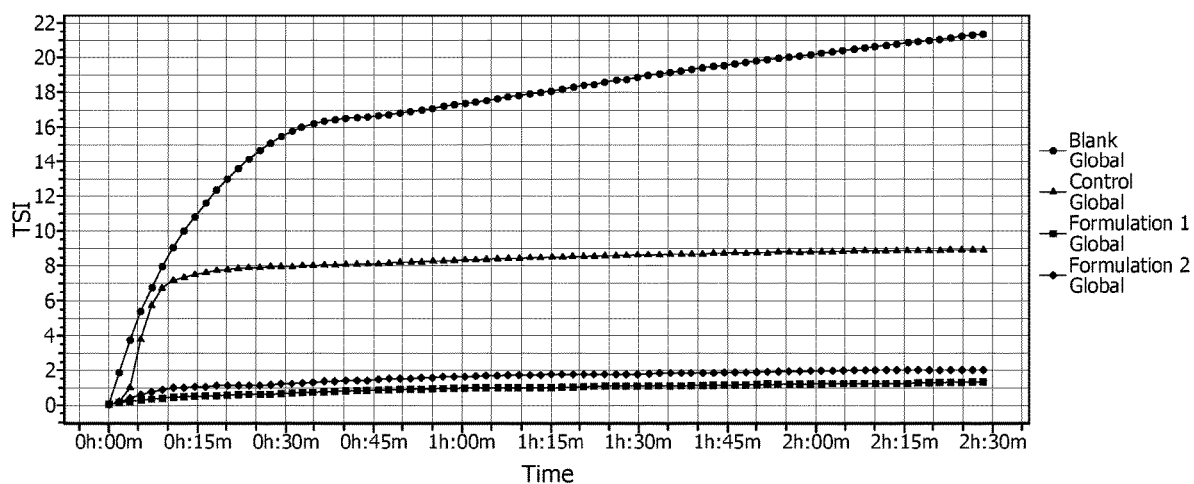
FIG. 2 is a graph providing results of an illustrative embodiment of the disclosed technology.

As shown in FIG. 2, the antifouling dispersant compositions (Formulation 1 and 2) in this invention effectively disperse the fouling materials HMB. The antifouling dispersant composition (50 ppm, 100 ppm) in this invention exhibit much better performances to effectively disperse the fouling materials HMB, as compared with 200 ppm of the control (Comparative Example 2).

Example 3

Table 3 provides a comparison on chemicals with different EO numbers:

TABLE 3

| Example | Chemistry |
|---|---|
| Compound D | Fatty alcohol (C12-C16) ethoxylate (EO = 3~7) |
| Comparative Example 3 | Fatty alcohol (C10-14) ethoxylate (EO = 20) |
| Comparative Example 4 | Fatty alcohol (C10-C16) ethoxylate (EO = 30) |
| Comparative Example 5 | Fatty alcohol (C12-16) ethoxylate (EO = 40) |
| Comparative Example 6 | Fatty alcohol (C14-18) ethoxylate (EO = 50) |
| Comparative Example 7 | Fatty alcohol (C16-18) ethoxylate (EO = 80) |

Figure 3:
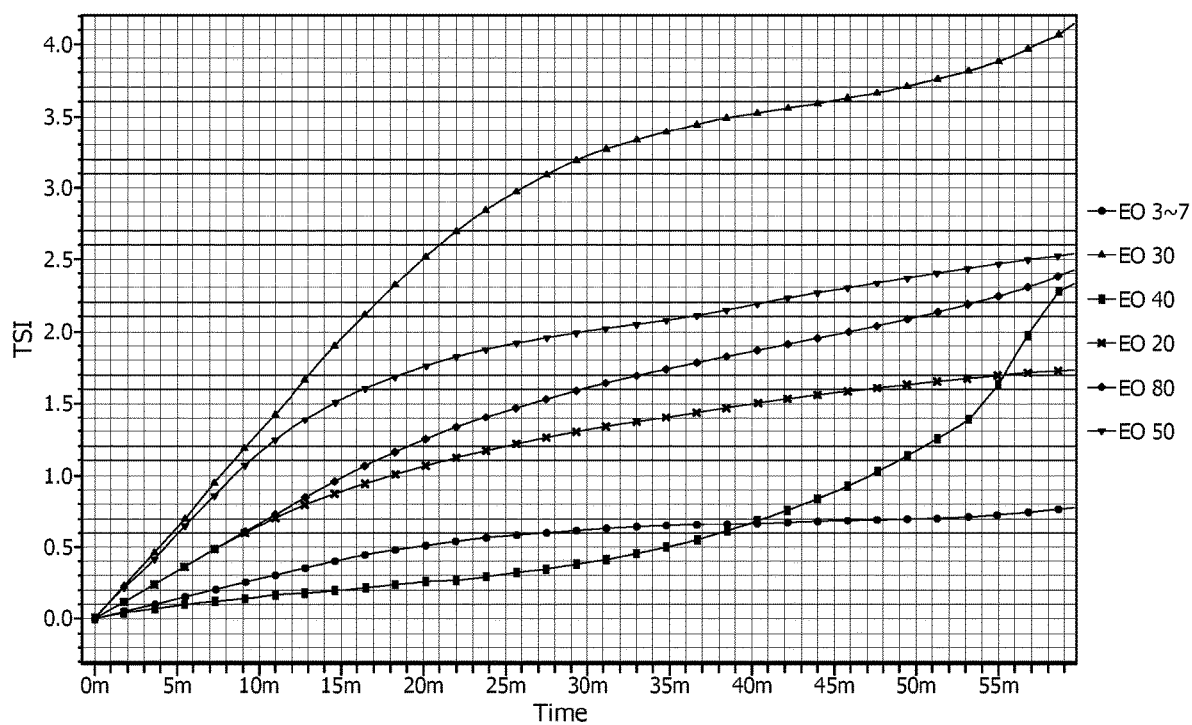
FIG. 3 is a graph providing results of an illustrative embodiment of the disclosed technology.

As shown in FIG. 3, the results indicate much better performance of the antifouling dispersant compound as provided in the disclosed technology to effectively disperse the fouling materials HMB than other higher EO fatty alcohol ethoxylate compounds. These results indicate that the antifouling dispersant compound as in the present disclosure exhibits significantly better performance to disperse the fouling materials of MTO water washing system than other higher EO fatty alcohol ethoxylate compounds which were mentioned as dispersants in prior arts.

While embodiments of the disclosed technology have been described, it should be understood that the present disclosure is not so limited and modifications may be made without departing from the disclosed technology. The scope of the disclosed technology is defined by the appended claims, and all devices, processes, and methods that come within the meaning of the claims, either literally or by equivalence, are intended to be embraced therein.

The invention claimed is:

1. A method of reducing fouling in olefin production system, the method comprising:
   adding an antifouling dispersant composition to an olefin production system, the antifouling dispersant composition comprising an alcohol polyoxyethylene (EO) ether (EO number 3-7), represented by the general formula $$R-O-(CH_2-CH_2-O)_n H, \qquad (I)$$

wherein R is an alkyl with about 12-16 carbon atoms; and n is 3-7; and
   one or more organic solvents comprising a glycol, a glycol ether, a glycerol or a pyrrolidone.

2. The method as recited in claim 1, wherein said olefin production system comprises an ethylene, propylene, isoprene, chloroprene, butylene (isomers thereof), isobutylene and butadiene, or a methanol-to-olefin (MTO) water washing system.

3. The method as recited in claim 1, wherein about 1-1000 ppm of the antifouling dispersant composition is added to a methanol-to-olefin (MTO) water washing tower.

4. The method as recited in claim 1, wherein the antifouling dispersant composition is continuously or intermittently injected into a MTO water washing tower.

5. The method as recited in claim 1, wherein the antifouling dispersant composition further comprises water.

6. The method as recited in claim 5, wherein the antifouling dispersant composition comprises about 0.1-95% water.

7. The method as recited in claim 1, wherein the antifouling dispersant composition comprises about 0.1-95% organic solvent.

8. The method as recited in claim 1, further comprising one or more alkyl phenolic resin ethoxylates, represented by the general formula (II)

wherein, $R_1$ is C3-C18 alkyl, the ethoxylate group (EO) number m is at a range of 1-50, the resin polymerization degree p is at a range of 0-20.

* * * * *